United States Patent [19]

Bandurco et al.

[11] Patent Number: 4,751,304

[45] Date of Patent: Jun. 14, 1988

[54] PROCESS FOR PREPARING 5,6-DIALKOXY-4-ALKYL-2(1H)-QUINAZOLINONES

[75] Inventors: Victor T. Bandurco, Bridgewater; Robert A. Mallory, Somerville; Jeffery B. Press, Rocky Hill, all of N.J.

[73] Assignee: Ortho Pharmaceutical Corporation, Raritan, N.J.

[21] Appl. No.: 654,820

[22] Filed: Sep. 26, 1984

[51] Int. Cl.$^4$ .......................................... C07D 239/80
[52] U.S. Cl. .................... 544/286; 544/284; 558/48; 558/52; 560/23; 560/29; 562/434; 260/543 R; 564/443; 568/337; 568/442
[58] Field of Search ........................................ 544/286

[56] References Cited

PUBLICATIONS

Brown, *Fused Pyrimidines*, Part I, Quinazolines, 1969, Interscience Publishers, N.Y. pp. 69–71.
Lucas, *Organic Chemistry*, 1953, Amer. Book Co., N.Y. pp. 209–219, 275–278, 421–423, 461–462.

*Primary Examiner*—Glennon H. Hollrah
*Assistant Examiner*—James H. Turnipseed
*Attorney, Agent, or Firm*—Benjamin F. Lambert

[57] ABSTRACT

A method for preparing 5,6-dialkoxy-4-alkyl-quinazolinones is described. The 5,6-dialkoxy-4-alkyl-quinazolinones are active cardiotonic agents.

11 Claims, No Drawings

PROCESS FOR PREPARING 5,6-DIALKOXY-4-ALKYL-2(1H)-QUINAZOLINONES

The present invention relates to a method of preparing 5,6-substituted quinazolinones. In particular, the invention relates to a process for preparing 5,6-dialkoxyquinazolinones of the formula

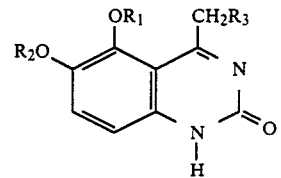

wherein $R_1$ and $R_2$ are the same or different lower alkyl having 1–4 carbon atoms and $R_3$ is hydrogen or lower alkyl having 1–4 carbon atoms, and their acid addition salts.

The process can be illustrated by the following schematic diagram in which the preparation of 5,6-dimethoxy-4-methyl-2(1H)-quinazolinone is exemplified.

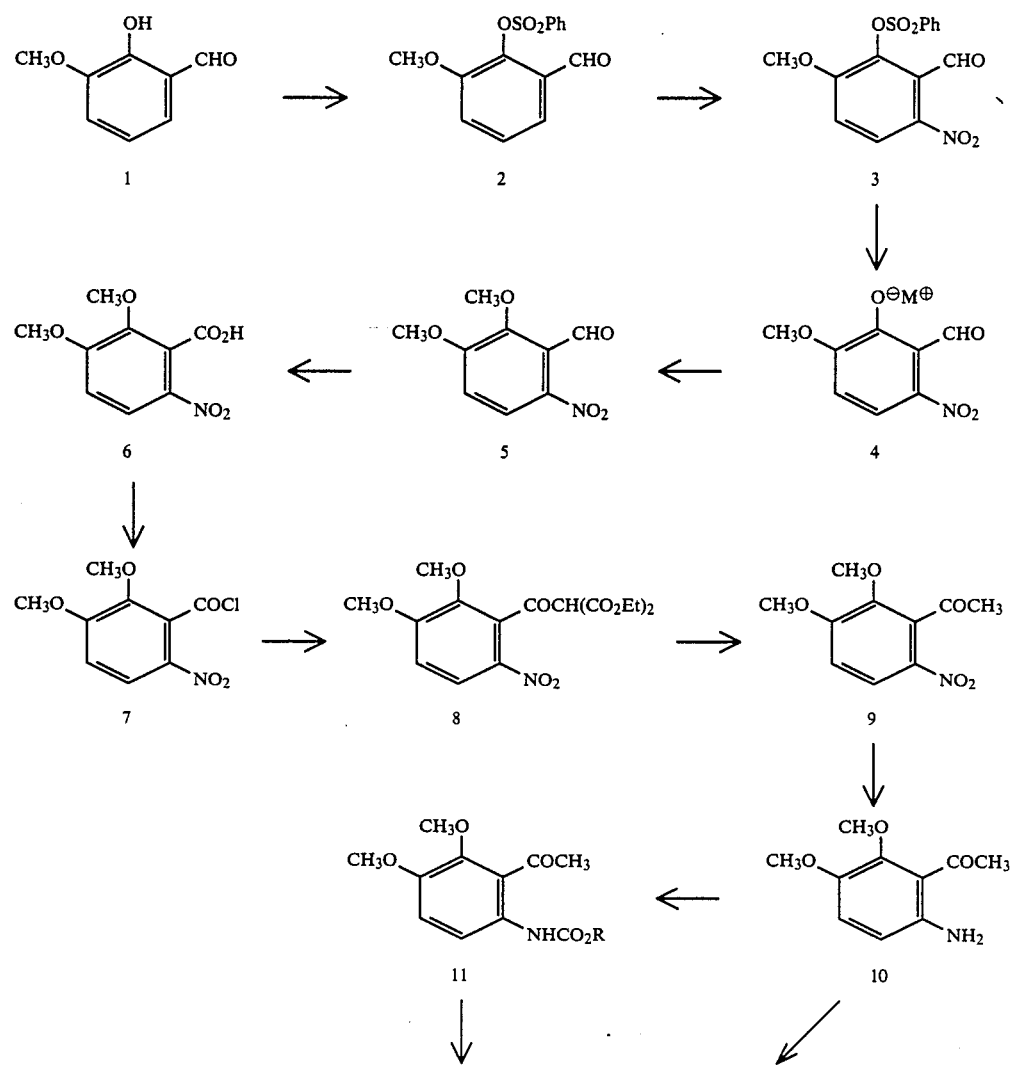

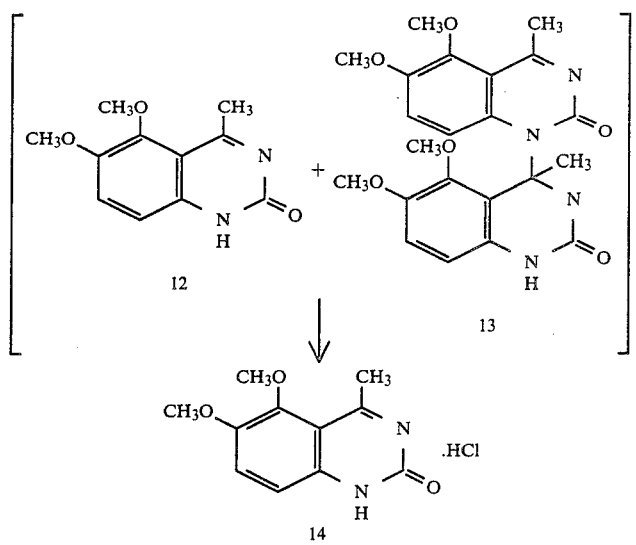

where $M^+ = K^+$, $Na^+$; $R$ = lower alkyl. The 5,6-dialkoxy quinazolinones of the present invention can be prepared by first reacting a 2-hydroxy-3-alkoxybenzaldehyde (1) with an aryl or alkylsulfonyl chloride such as, for example, benzenesulfonyl chloride, methylsulfonyl chloride, p-toluenesulfonyl chloride and 4-chlorobenzenesulfonyl chloride to form the corresponding alkyl or arylsulfonate (2). The reaction is carried out at room temperature in a suitable solvent such as, for example, methylene chloride, chloroform or ether in the presence of a base such as potassium hydroxide or sodium hydroxide. The aryl or alkylsulfonate is then nitrated with a nitrating agent such as nitric acid to form the corresponding 6-nitrobenzaldehyde aryl or alkylsulfonate (3). The nitration reaction is carried out at temperatures between about 0° C. and ±2° C. The product is isolated by techniques known to those skilled in the art. The 6-nitrobenzaldehyde alkyl or arylsulfonate is then converted to a salt by treatment with a strong base. Bases which can be employed include alkali and alkaline earth metal hydroxides. The reaction may be carried out at room temperature but it is preferred to carry out the reaction at the reflux temperature of the solvents. Suitable solvents for the reaction include methanol, ethanol, propanol and n-butanol. The salt is then converted to the dialkoxy-6-nitrobenzaldehyde (5) by reaction with the appropriate dialkyl sulfate such as dimethyl sulfate, diethyl sulfate, dibutyl sulfate, etc. The reaction may be carried out at room temperature but it is preferred to carry out the reaction at the reflux temperature of the solvent. Suitable solvents which can be employed include acetone, tetrahydrofuran and dioxane. The corresponding dialkoxy-6-nitrobenzoic acid compound (6) is then prepared by reacting the aldehyde (5) with an oxidizing agent such as potassium permanganate and oxides of chromium, in a suitable solvent such as acetone, tetrahydrofuran and dioxane. The reaction can be carried out at a temperature between room temperature and about 75° C. The preferred reaction temperature is about 50° C. The free acid (6) is then converted to its propanedioate ester (8) by first reacting the acid (6) with a chlorinating agent such as thionyl chloride and phosphorous oxychloride to form the corresponding acid halide (7) and then converting the acid halide (7) to the ester (8) by reaction with diethylmalonate or an alkyldiethylmalonate such as methyl diethylmalonate, ethyl diethylmalonate or butyl diethylmalonate. The formation of the acid halide (7) is carried out preferably at reflux temperature of the reaction mixture. The acid halide (7) can be used in the next step without first isolating it. The ester (8) is prepared by reacting the acid halide (7) with a Grignard reagent prepared from diethylmalonate or an alkyl diethylmalonate such as methyl diethylmalonate, ethyl diethylmalonate or propyl diethylmalonate and magnesium by techniques known to those skilled in the art. The reaction with the Grignard reagent is preferably carried out at the reflux temperature of the solvent although temperatures between 40° C. and 60° C. may also be employed. Suitable solvents for the reaction include toluene, ether, tetrahydrofuran and dioxane. The ester (8) is then converted to the corresponding ketone (9) by reaction with an acid, such as acetic acid and sulfuric acid. The reaction is carried out at elevated temperatures between about 30°–100° C. and preferably at the reflux temperature of the reaction mixture. When acetic acid is employed as the solvent the reaction is catalyzed by the presence of a strong acid such as, for example, sulfuric acid. The ketone (9) is isolated by techniques known to those skilled in the art. Catalytic reduction of the alkyl 2,3-dialkoxy-6-nitrophenyl ketone (9) with a reducing agent such as hydrogen on palladium or platinum oxide in a suitable solvent such as methanol gives the corresponding alkyl 6-amino-2,3-dialkoxyphenyl ketone (10). The reaction can also be carried out non-catalytically with iron/acetic acid. Reaction of the amine (10) with an isocyanate such as potassium isocyanate at a temperature between about 20°–35° C. and in a suitable solvent such as acetic acid, for example, gives a mixture of the 2,3-dialkoxyquinazolinone (12) and its dimer (13). The quinazolinone hydrochloride salt (14) is separated from the dimer by heating the mixture at a temperature between 70°–120° C. in the presence of concentrated mineral acid such as, for example, concentrated hydrochloric acid. The quinazolinone is isolated as the acid or hydrochloride salt (14) by techniques known to those skilled in the art. The quinazolinone (14) can also be obtained by heating the dimer (13) at temperatures between about 70°–170° C. in the presence of hydrochloric acid.

Alternatively the quinazolinone (14) can be obtained by reacting the amine (10) first with an alkyl chloroformate such as ethyl-, methyl- or butylchloroformate, for example, in a suitable solvent such as ether, dioxane or tetrahydrofuran to form the corresponding carbamate (11) which is then treated with ammonium acetate at temperatures ranging from about 100°–150° C., preferably 125°–130° C., to form a mixture of the quinazolinone (12) and its dimer (13). The quinazolinone can be isolated as its hydrochloride salt (14) by treating the mixture with hydrochloric acid at elevated temperatures. The free 5,6-dialkoxy-4-alkyl-2(1H)-quinazolinone (12) is obtained by treating the hydrochloride salt with aqueous alkali by techniques known to those skilled in the art.

Those compounds wherein $R_1$ and $R_2$ are other than methyl and $R_3$ is other than hydrogen are prepared in the same manner as illustrated in the following examples by using an appropriately substituted benzaldehyde, alkyl sulfate and alkyl diethylmalonate in the reaction scheme. The 5,6-dialkoxy-4-alkyl-2(1H)-quinazolinones are active cardiotonic agents.

EXAMPLE 1

2-Hydroxy-3-methoxybenzaldehyde benzenesulfonate

A solution of o-vanillin (537.5 g, 3.54 mole) in water (3.6 L) containing potassium hydroxide (215 g, 3.77 mole) was treated with benzenesulfonyl chloride (360 mL, 2.83 mole) dropwise over a period of one hour. Methylene chloride (75 ml) was added and the mixture was stirred overnight. The resultant solid was collected by filtration and washed with 500 mL of 5% aqueous potassium hydroxide and 1 L of water. The solid was dried in vacuo at 70°–90° C. to give the title compound, 750 g, mp 115°–119° C.

EXAMPLE 2

2-Hydroxy-3-methoxy-6-nitrobenzaldehyde benzenesulfonate

2-Hydroxy-3-methoxybenzaldehyde benzenesulfonate (200 g, 0.685 mole) was added to 90% nitric acid (400 mL) with the temperature maintained at 0°±2° over a period of onehalf to one hour. The reaction mixture was stirred an additional 0.5 hour and poured over ice (2.5 L) with stirring. After standing several hours, the solid was collected by filtration and washed with water (500 mL). The solid was then suspended in acetone (1.25 L) and the mixture was heated to reflux for 0.5 hour, concentrated to 500 mL and cooled to 15° C. The resultant solid was collected by filtration and washed with cold acetone (125 mL) to provide the title compound, 138.5 g (60%), mp 151–155° C.

EXAMPLE 3

2-Hydroxy-3-methoxy-6-nitrobenzaldehyde potassium salt

2-Hydroxy-3-methoxy-6-nitrobenzaldehyde benzenesulfonate (80.0 g, 0.237 mole) was slurried in methanol (4.0 L) and heated to reflux. Aqueous potassium hydroxide (51.2 g in 110 mL) was added with stirring to the refluxing solution over 0.5 hour and heating was continued an additional 0.5 hour. The thick paste which formed was cooled to room temperature and filtered to give the product as a vermillion solid, 52.8 g (95%). This material was not further purified but carried on to the next step.

EXAMPLE 4

2,3-Dimethoxy-6-nitrobenzaldehyde

2-Hydroxy-3-methoxy-6-nitrobenzaldehyde potassium salt was slurried in acetone (500 mL) containing potassium carbonate (50 g) and the suspension was treated with dimethylsulfate (18.5 mL) and heated to reflux for one hour. An additional aliquot (18.5 mL) of dimethylsulfate was then added and the mixture was heated overnight. After 24 hours the red color of the potassium salt was virtually absent. The salts were removed by filtration, the filtrate was concentrated and the residue was recrystallized from isopropanol to give the title compound 40.0 g (80% from 3) mp 109°–110° C.

EXAMPLE 5

2,3-Dimethoxy-6-nitrobenzoic acid 2,3-Dimethoxy-6-nitrobenzaldehyde (40.0 g, 0.19 mole) was treated with acetone (275 mL) and warmed to 50° C. A solution of potassium permanganate in water (60 g/L) was added slowly at 50°–70° C. over a period of 16–20 hours until thin layer chromatographic analysis revealed complete absence of the starting material. Isopropanol (7.5 mL) was then added and the mixture was heated an additional hour. The precipitated manganese dioxide was removed by filtration and the filter cake was washed with 3% aqueous potassium hydroxide (ca 175–200 mL). The combined filtrates were acidified with hydrochloric acid and the precipitate was collected by filtration and dried in vacuo. The crude product was recrystallized from acetone to give the pure material, 28.3 g (67%), mp 187°–189° C.).

EXAMPLE 6

Diethyl 2-(2,3-dimethoxy-6-nitrobenzoyl)propanedioate (a) 2,3-Dimethoxy-6-nitrobenzoic acid (25 g, 0.11 mole) was added to thionyl chloride (50 mL) and the mixture was heated to reflux for 3 hours. Excess thionyl chloride was removed by distillation, the residue was triturated with toluene (50 mL) and the solvent was removed again by distillation. The resulting 2,3-dimethoxy-6-nitrobenzoyl chloride was dissolved in toluene (40 mL) and diethyl ether (40 mL).

(b) Grignard quality magnesium (3.04 g, 0.125 mole) was treated with absolute ethanol (3.1 mL) and carbon tetrachloride (0.5 mL) and diethyl ether (100 mL) was added once vigorous reaction began. A solution of diethylmalonate (23.4 g, 0.146 mole) in ether (18 mL) and ethanol (14 mL) was added over 1 hour maintaining reflux. The mixture was heated at reflux an additional 3 hours. The reaction solution was then diluted with toluene (40 mL) and ether (80 mL).

(c) The acid chloride solution from (a) above was then added to the magnesium salt solution over a period of 0.5 hour at reflux and the entire mixture was heated an additional 3 hours. After cooling to 15° C., the solid that precipitated was collected by filtration; this solid was then added to 10% sulfuric acid (125 mL) and the resultant aqueous solution was extracted with methylene chloride. The methylene chloride layers were dried over magnesium sulfate and concentrated to give the diester, 53.75 g (95%), mp 71°–73° C.

EXAMPLE 7

2,3-Dimethoxy-6-nitroacetophenone

Diethyl 2-(2,3-dimethoxy-6-nitrobenzoyl)propanedioate diester (53.57 g, 0.105 mole) was heated to reflux in 60% aqueous acetic acid (60 mL) containing sulfuric acid (4.25 mL) for 7 hours. Aqueous sodium hydroxide (4 g in 8 mL of water) was added slowly with cooling and the solution was concentrated to an oil. This residue was dissolved in methylene chloride, decolorized with charcoal, evaporated and recrystallized from isopropanol to give the title compound, 22.5 g (100%), mp 66°–67° C.

EXAMPLE 8

6-Amino-2,3-dimethoxyacetophenone 2,3-Dimethoxy-6-nitroacetophenone (20.0 g, 0.089 mole) dissolved in methanol (100 mL) containing 10% palladium-carbon catalyst was treated with excess hydrogen at a pressure of 1–4 atmospheres until hydrogen was no longer absorbed. The catalyst was removed by filtration, the filtrate concentrated and the residue was recrystallized from isopropanol to give the title compound, 16.25 g (94%), mp 59°–61° C.

EXAMPLE 9

5,6-Dimethoxy-4-methyl-2(1H)-quinazolinone Hydrochloride Hydrate

6-Amino-2,3-dimethoxyacetophenone (15.00 g, 0.077 mole) in acetic acid (375 mL) was treated with potassium isocyanate (15 g) portionwise over 1–3 hours. The mixture was stirred under nitrogen atmosphere at 25°–35° C. for 16 hours. The precipitate was collected by filtration, washed with water (100 mL) and acetone (100 mL) and air dried to give a solid 12.6 g (74%). The solid was suspended in water (175 mL), warmed to 70° C. and concentrated hydrochloric acid (175 mL) was added. The temperature was raised to 110° C. until complete solution occurred. Hot filtration, subsequent cooling to 15° C. with stirring and filtration of the resulting precipitate provided the title compound as yellow crystals. Washing with 6 N hydrochloric acid (30 mL) and acetone (120 mL) and drying gave 12.68 g (71%) of the hydrate of 5,6-dimethoxy-4-methyl-2(1H)-quinazolinone hydrochloride, mp 203°–205° C.

Alternatively the solid was suspended in concentrated hydrochloric acid (160 mL) and heated to 30°–38° C. until complete solution occurred. The solution was filtered, diluted with water (160 mL) and cooled to 15° C. The resulting precipitate was collected by filtration, washed with acetone and dried to give 14 (16.9 g, 95%).

EXAMPLE 10

5,6-Dimethoxy-4-methyl-2(1H)-quinazolinone Hydrochloride hydrate

6-Amino-2,3-dimethoxyacetophenone (48.0 g, 0.246 mole) dissolved in tetrahydrofuran (370 mL) was treated with ethyl chloroformate (59.1 mL) over a period of 1 hour at 0° C. After 30 minutes, a solution of sodium hydroxide (22.9 g) in water (85 mL) was added to the mixture over 30 minutes. After additional stirring for 1 hour, the mixture was filtered, and the upper layer of the filtrate was separated and evaporated in vacuo. The lower layer of the filtrate was extracted with methylene chloride and this phase was added to the residue from the upper layer. Concentration and recrystallization of the residue from isopropanol gave ethyl 2,3-dimethoxyacetophenone-6-carbamate, 65.9 g (100%), mp 63°–65° C. This material was placed in a flask, covered with ammonium acetate (365 g) and the mixture was heated in an oil bath until a clear melt was obtained. Stirring and heating of the melt at 125°–130° C. for 2 hours followed by quenching of the molten reaction in 2 L of water gave a solid (a mixture of 12 and 13), 40 g (74%), after drying of the filtered precipitate. This mixture was treated with concentrated hydrochloric acid at 50° C. as above to give the hydrate of 5,6-dimethoxy-4-methyl-2(1H)-quinazolinone hydrochloride, 35 g (71%), mp 204°–206° C.

EXAMPLE 11

5,6-Dimethoxy-4-methyl-2(1H)-quinazolinone 5,6-Dimethoxy-4-methyl-2(1H)-quinazolinone hydrochloride (4.26 g) was dissolved in water (500 mL) and 30% aqueous sodium hydroxide was added to adjust the pH to 7. The precipitate was collected to give 5,6-dimethoxy-4-methyl-2(1H)-quinazolinone as a yellow crystalline solid, mp 248°–249° C.

We claim:

1. The process for the preparation of a compound of the formula:

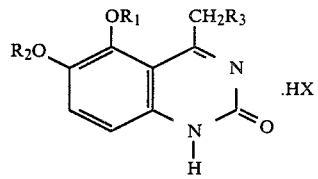

which comprises reacting a compound of the formula

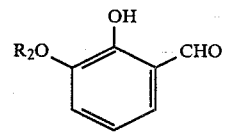

with an alkyl or arylsulfonyl chloride to form a compound of the formula

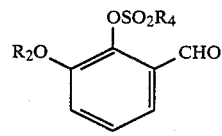

reacting the product with nitric acid to form a nitrobenbzaldehyde of the formula

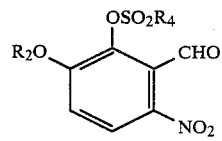

treating the nitrobenzaldehyde alkyl or arylsulfonate with an alkali metal hydroxide to form a salt of the formula 4,751,304

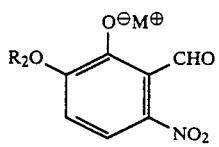

reacting the salt formed with a dialkylsulfate to form a nitrobenzaldehyde of the formula

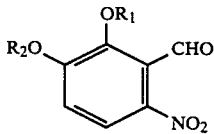

reacting the nitrobenzaldehyde with an oxidizing agent to form a nitrobenzoic acid of the formula

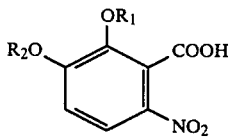

reacting the nitrobenzoic acid with a chlorinating agent to form an acid halide of the formula

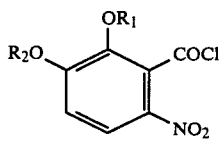

reacting the acyl halide with a Grignard reagent prepared from magnesium and diethylmalonate or an alkyl diethylmalonate to form a diester of the formula

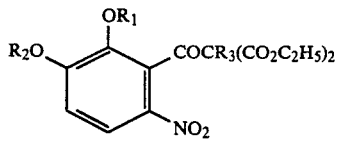

reacting the diester with acid to form an alkyl nitrophenyl ketone of the formula

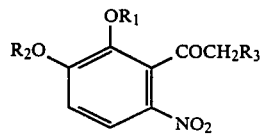

reacting the alkyl nitrophenyl ketone with a reducing agent to form an alkyl aminophenyl ketone of the formula

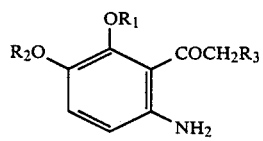

reacting the amine with an alkyl chloroformate to form a carbamate of the formula

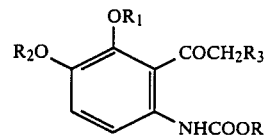

treating the carbamate with ammonium acetate and treating the mixture formed with a mineral acid, wherein $R_1$ and $R_2$ are the same or different lower alkyl, $R_3$ is hydrogen or lower alkyl, $R_4$ is aryl or alkyl, R is lower alkyl, and $M^+$ is a cation selected from potassium and sodium, and X is chloro or bromo.

2. The process of claim 1 which additionally comprises treating the hydrochloride salt with an aqueous alkali metal hydroxide to form the free quinazolinone.

3. The process of claim 1 wherein the alkyl and arylsulfonyl chloride are selected from benzenesulfonyl chloride, methylsulfonyl chloride p-toluenesulfonyl chloride and 4-chlorobenzenesulfonyl chloride.

4. The process of claim 1 wherein the alkali metal hydroxide is selected from potassium hydroxide and sodium hydroxide.

5. The process of claim 1 wherein the oxidizing agent is potassium permanganate.

6. The process of claim 1 wherein the chlorinating agent is thionyl chloride.

7. The process of claim 1 wherein the isocyanate is potassium isocyanate.

8. The process of claim 1 wherein the reducing agent is hydrogen, the alkyl chloroformate is ethyl chloroformate and the mineral acid is hydrochloric acid.

9. The process of claim 1 wherein the dialkylsulfate is dimethylsulfate, $R_1$ and $R_2$ are methyl and $R_3$ is hydrogen.

10. The process according to claim 1 for the preparation of a compound of the formula

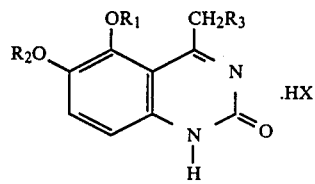

which comprises reacting an alkyl nitrophenyl ketone of the formula

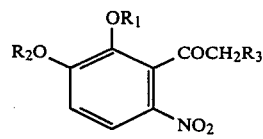

with a reducing agent to form an alkyl aminophenyl ketone of the formula

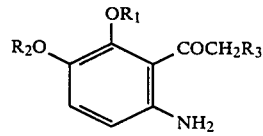

reacting the alkyl aminophenyl ketone with an alkyl chloroformate to form a carbamate of the formula

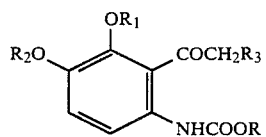

reacting the adduct with ammonium acetate and treating the mixture formed with a mineral acid, wherein $R_1$ and $R_2$ are the same or different lower alkyl, $R_3$ is hydrogen or lower alkyl, and R is lower alkyl, and X is chloro or bromo.

11. The process of claim 10 which additionally comprises treating the hydrochloride salt with aqueous sodium hydroxide to form the free quinazolinone.

* * * * *